(12) United States Patent
Lin et al.

(10) Patent No.: US 10,569,096 B2
(45) Date of Patent: Feb. 25, 2020

(54) STATIONARY TRANS-SKULL OPTOGENETIC STIMULATION MODULE

(71) Applicant: NATIONAL CHENG KUNG UNIVERSITY, Tainan (TW)

(72) Inventors: Chou-Ching Lin, Tainan (TW); Chia-Chu Chiang, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 563 days.

(21) Appl. No.: 15/369,953

(22) Filed: Dec. 6, 2016

(65) Prior Publication Data

US 2018/0154169 A1 Jun. 7, 2018

(51) Int. Cl.
*A61N 5/06* (2006.01)

(52) U.S. Cl.
CPC ......... *A61N 5/0601* (2013.01); *A61N 5/0622* (2013.01); *A61N 2005/0612* (2013.01); *A61N 2005/0651* (2013.01)

(58) Field of Classification Search
CPC .......... A61N 5/00; A61N 5/06; A61N 5/0601; A61N 5/0613; A61N 5/0618; A61N 5/0622; A61N 2005/063
See application file for complete search history.

(56) References Cited

U.S. PATENT DOCUMENTS

| 8,781,575 | B2 | 7/2014 | de Vos et al. | |
|---|---|---|---|---|
| 8,977,361 | B2 | 3/2015 | Carpentier et al. | |
| 2007/0027483 | A1 | 2/2007 | Maschino et al. | |
| 2014/0058483 | A1 | 2/2014 | Zao et al. | |
| 2015/0217133 | A1* | 8/2015 | Angeley | A61N 5/062 607/91 |
| 2017/0199364 | A1* | 7/2017 | Doric | G02B 21/082 |

FOREIGN PATENT DOCUMENTS

| CN | 101657230 A | 2/2010 |
|---|---|---|
| CN | 103002950 A | 3/2013 |
| TW | 201416060 A | 5/2014 |

* cited by examiner

*Primary Examiner* — Allen Porter
(74) *Attorney, Agent, or Firm* — Mark M. Friedman

(57) ABSTRACT

A stationary trans-skull optogenetic stimulation module is provided and includes a sleeve to be inserted and positioned in a drilled hole of a skull of a subject, an optogenetic stimulating element, and a cover. The sleeve has a large aperture portion and a small aperture portion, and the optogenetic stimulating element and the cover can be installed with or disassembled from the large aperture portion. Thus, the operation time of syringe injection and phototherapeutic irradiation can be reduced, and the operation efficiency can be increased.

9 Claims, 7 Drawing Sheets

STATIONARY TRANS-SKULL OPTOGENETIC STIMULATION MODULE

FIELD OF THE INVENTION

The present invention relates to an optogenetic stimulation module, and more particularly to a stationary trans-skull optogenetic stimulation module.

BACKGROUND OF THE INVENTION

Epilepsy is a chronic neurological disorder presenting a wide spectrum of diseases, and a neurological condition characterized by recurrent seizures. These seizures are transient signs and/or symptoms due to abnormal, excessive or synchronous neuronal activity in the brain. Epilepsy should not be understood as a single disorder, but rather as a group of syndromes with vastly divergent symptoms but all involving episodic abnormal electrical activity in the brain.

Epilepsy is one of the most serious neurological disorders, and requires long-term treatment. There are many clinical methods to treat epilepsy, such as medical treatment, resection surgery, and electrical stimulation. However, the technology of the optogenetic stimulation is a new method for the treatment of epilepsy developed recently, wherein the technology of the optogenetic stimulation can excite or inhibit the neurons with a photographic protein by irradiating. Therefore, the optogenetic stimulation can control specific neurons, and not affect other neurons, and has less side effects compared with electrical stimulation. In addition, the optogenetic stimulation can also help to explore the inhibition for epilepsy. However, how to pass through a skull and effectively implement the optogenetic stimulation on the neurons, or how to conveniently and frequently process the treatment of the optogenetic stimulation, are technical problems that must be solved at present.

As a result, it is necessary to provide a developed stationary trans-skull optogenetic stimulation module to solve the problems existing in the conventional technologies, as described above.

SUMMARY OF THE INVENTION

An object of the present invention is to provide a stationary trans-skull optogenetic stimulation module, wherein an optogenetic stimulating element and a cover can be quickly and conveniently installed with or disassembled from the large aperture portion, and the operation time of syringe injection and phototherapeutic irradiation can be reduced, and the operation efficiency can be increased.

To achieve the above object, the present invention provides a stationary trans-skull optogenetic stimulation module, which comprises a sleeve, an optogenetic stimulation element, and a cover; wherein the sleeve is configured to be inserted and positioned in a drilled hole of a skull of a subject, and including a small aperture portion, a large aperture portion and an inner flange, the small aperture portion is communicated with the large aperture portion, and the inner flange is disposed between the small aperture portion and the large aperture portion; the optogenetic stimulation element includes a connection portion configured to be detachably connected with the large aperture portion, an extension portion extended from the connection portion into the small aperture portion, a through hole passing through the connection portion and the extension portion, and an illuminator disposed on the extension portion; the cover is configured to be connected with the large aperture portion and covers the connection portion.

In one embodiment of the present invention, the illuminator includes a light emitting diode or a spiral light strip.

In one embodiment of the present invention, the illuminator is further covered with a biocompatible silicone layer.

In one embodiment of the present invention, the optogenetic stimulation element further includes a fixation base disposed in the through hole, and configured to fix the illuminator.

In one embodiment of the present invention, the optogenetic stimulation element further includes: a sealing groove formed on a top surface of the connection portion, and two conductive portions disposed in the sealing groove and electrically connected to the illuminator.

In one embodiment of the present invention, the cover includes a top surface and at least one depressed portion formed on the top surface.

In one embodiment of the present invention, the stationary trans-skull optogenetic stimulation module further comprises an elastic ring configured to be installed between the inner flange and the connection portion.

In one embodiment of the present invention, the cover and the connection portion and the extension portion of the optogenetic stimulation element are made of titanium or titanium alloy.

In one embodiment of the present invention, the connection portion is formed with a first external thread portion, the large aperture portion is formed with an internal thread portion, and the internal thread portion is configured to be screw-connected to the first external thread portion.

In one embodiment of the present invention, the cover includes a second external thread portion, and the internal thread portion is configured to be further screw-connected to the second external thread portion.

As described above, the syringe passes through the through hole and the small aperture portion and injects the designated area in the skull with a carrier of photoreceptor gene by inserting the sleeve in the drilled hole, and then the optogenetic stimulation is implemented on the designated area by using the illuminator for generating a reaction from the designated area. Thus, the optogenetic stimulating element and the cover can be quickly and conveniently installed with or disassembled from the large aperture portion, and the operation time of syringe injection and phototherapeutic irradiation can be reduced, and the operation efficiency can be increased.

DETAILED DESCRIPTION OF THE PREFERRED EMBODIMENTS

The structure and the technical means adopted by the present invention to achieve the above and other objects can be best understood by referring to the following detailed description of the preferred embodiments and the accompanying drawings. Furthermore, directional terms described by the present invention, such as upper, lower, front, back, left, right, inner, outer, side, longitudinal/vertical, transverse/horizontal, etc., are only directions by referring to the accompanying drawings, and thus the used directional terms are used to describe and understand the present invention, but the present invention is not limited thereto.

Figure 1:
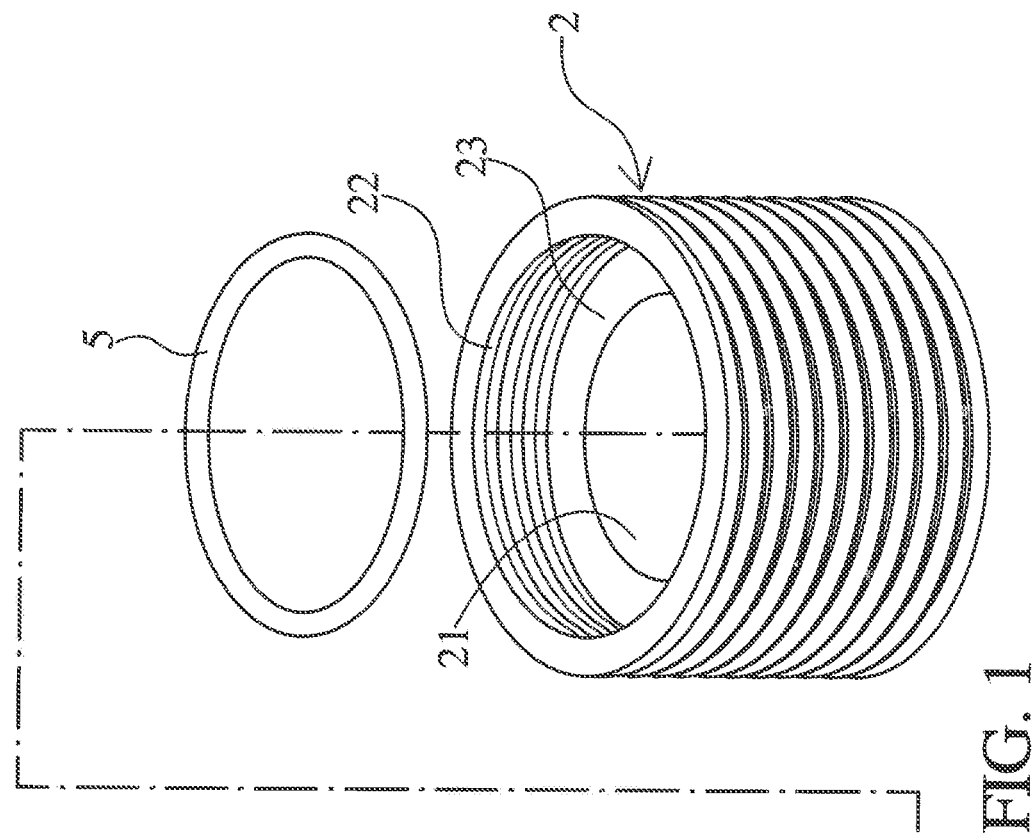
FIG. 1 is a schematic view of a stationary trans-skull optogenetic stimulation module according to a first embodiment of the present invention.
Figure 1:
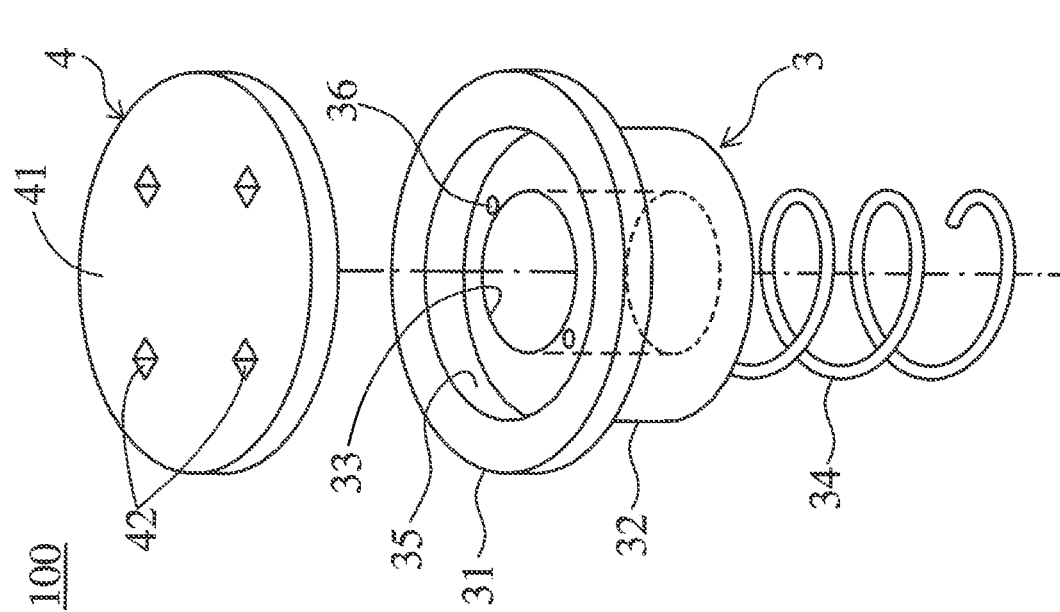
Figure 2:
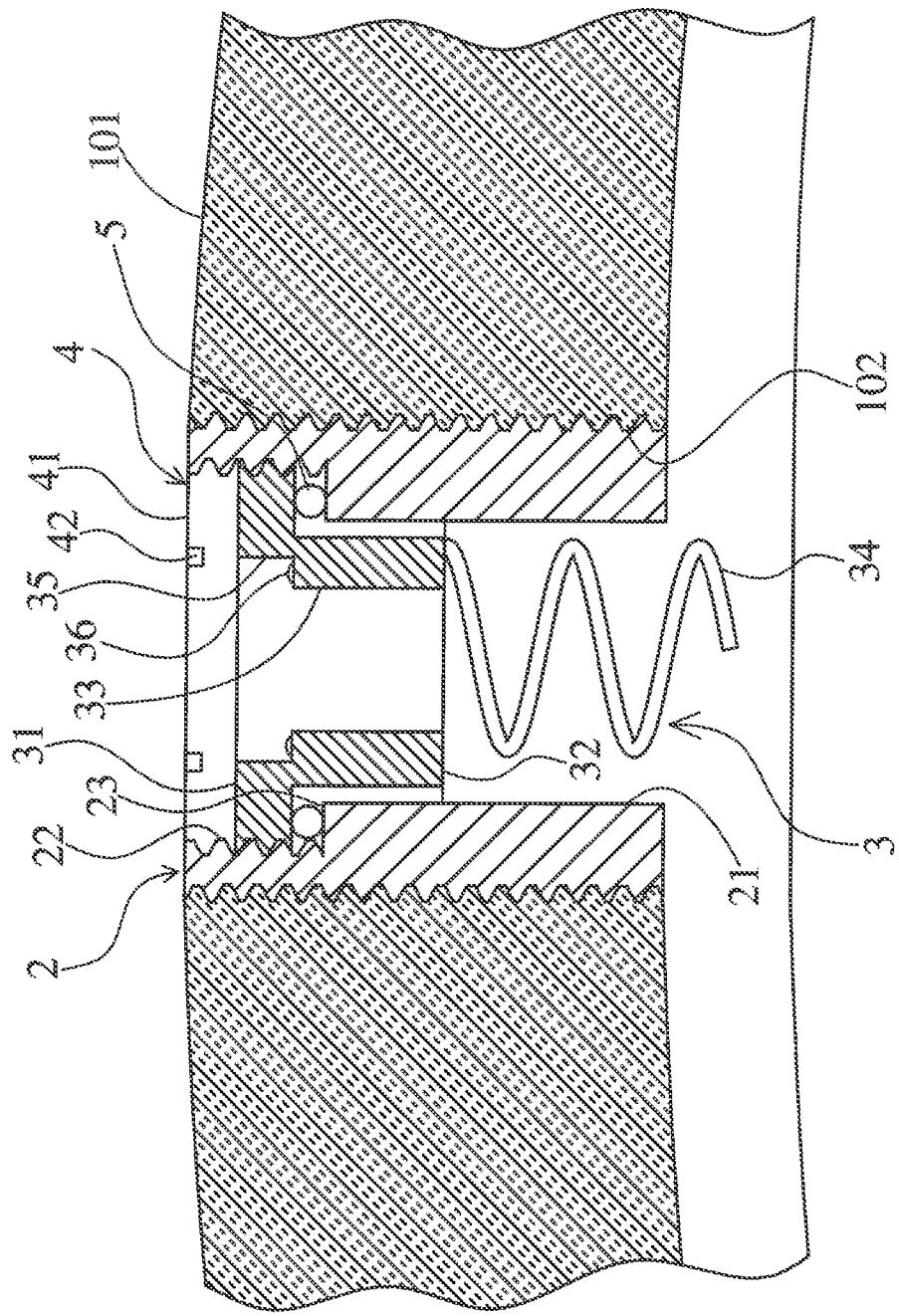
FIG. 2 is a sectional view of a stationary trans-skull optogenetic stimulation module according to the first embodiment of the present invention.

Referring to FIGS. 1 and 2, a stationary trans-skull optogenetic stimulation module according to a first embodiment of the present invention is illustrated, which is installed on a skull 101 of a subject, such as human beings or animals. As shown, the stationary trans-skull optogenetic stimulation module 100 comprises a sleeve 2, an optogenetic stimulation element 3, a cover 4, and an elastic ring 5. The detailed structure of each component, assembly relationships, and principles of operation in the present invention will be described in detail hereinafter.

Referring to FIGS. 1 and 2, the sleeve 2 is configured to be inserted and positioned in a drilled hole 102 of the skull 101, and the sleeve 2 includes a small aperture portion 21, a large aperture portion 22, and an inner flange 23. Referring to FIG. 2, the small aperture portion 21 is communicated with the large aperture portion 22, and the inner flange 23 is disposed between the small aperture portion 21 and the large aperture portion 22.

Referring to FIGS. 1 and 2, the optogenetic stimulation element 3 includes a connection portion 31, an extension portion 32, a through hole 33, an illuminator 34, a sealing groove 35, and two conductive portions 36, wherein the connection portion 31 is configured to be detachably connected with the large aperture portion 22, and the extension portion 32 is extended from a bottom surface of the connection portion 31 into the small aperture portion 21, and the through hole 33 passes through the connection portion 31 and the extension portion 32 along a geometric center of the connection portion 31, and the illuminator 34 is disposed on a bottom surface of the extension portion 32 and the illuminator 34 electrically connects to the conductive portions 36, and the sealing groove 35 is formed on a top surface of the connection portion 31, and the conductive portions 36 are disposed in the sealing groove 35 and electrically connected to the illuminator 34. In the embodiment of the present invention, the illuminator 34 includes a spiral light strip, such as a section of fiber, and the illuminator 34 is further covered with a biocompatible silicone layer.

Figure 3:
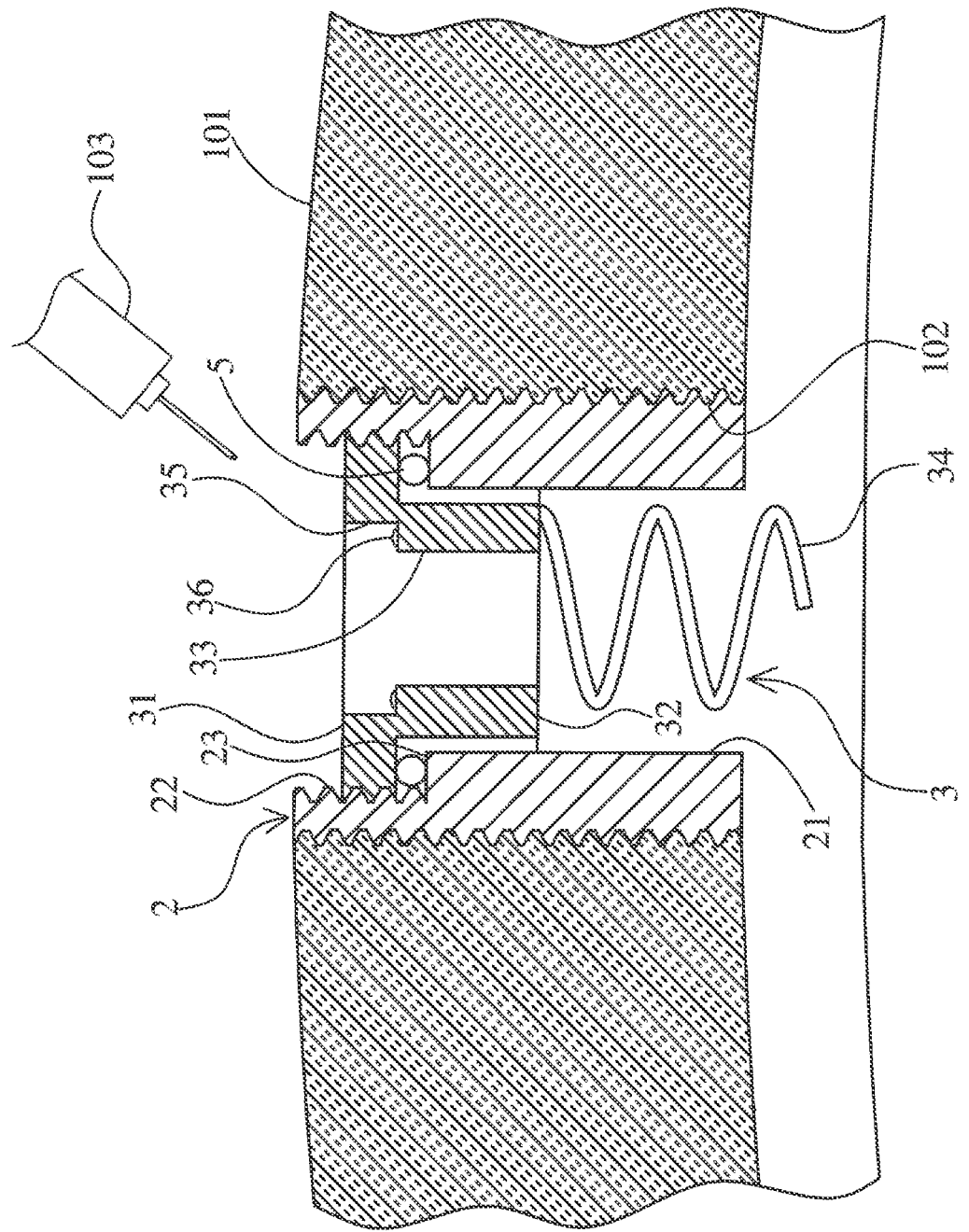
FIG. 3 is a sectional view of a stationary trans-skull optogenetic stimulation module for implementation according to the first embodiment of the present invention.

Referring to FIGS. 1 and 3 of the embodiment of the present invention, the connection portion 31 is formed with a first external thread portion, and the large aperture portion 22 is formed with an internal thread portion, wherein the internal thread portion of the large aperture portion 22 is configured to be screw-connected to the first external thread portion of the connection portion 31, and the cover 4, and the connection portion 31 and the extension portion 32 of the optogenetic stimulation element 3 are made of titanium or titanium alloy.

Referring to FIGS. 1 and 2, the cover 4 is configured to be connected with the large aperture portion 22 of the sleeve 2, and the cover 4 covers the connection portion 31 and is located in the sealing groove 35, wherein the cover 4 includes a top surface 41 and a plurality of depressed portions 42, the depressed portions (or a depressed portion) are formed on the top surface 41. In the embodiment of the present invention, a second external thread portion is formed on the cover 4, and the internal thread portion of the large aperture portion 22 is configured to be screw-connected to the second external thread portion of the cover 4, thus the cover 4 seals the sealing groove 35 and the through hole 33.

Referring to FIGS. 1 and 2, the elastic ring 5 is configured to be installed between the inner flange 23 of the sleeve 2 and the connection portion 31 of the optogenetic stimulation element 3. In the embodiment of the present invention, the elastic ring 5 is made of a biocompatible silicone.

The internal thread portion is configured to be further screw-connected to the second external thread portion to avoid liquid leakage from the through hole 33.

According to the described structure and referring to FIG. 2, the sleeve 2 is inserted and positioned in the drilled hole 102 of the skull 101 for sequentially screw-connecting to the optogenetic stimulation element 3 and the cover 4 in the large aperture portion 22 of the sleeve 2, and the cover 4 is covered on the connection portion 31 of the optogenetic stimulation element 3. Referring to FIG. 3, the depressed portions 42 can be engaged by a tool for unfastening the cover 4, and the cover 4 can be disassembled from the large aperture portion 22 of the sleeve 2. At this time, a syringe 103 can be used to pass through the through hole 33 and the small aperture portion 21, and injects a designated area in the skull 101 with a carrier of photoreceptor gene, and the optogenetic stimulation (phototherapeutic irradiation) is implemented on the designated area by using the illuminator 34 (spiral light strip) located at the small aperture portion 21, wherein the optogenetic stimulation adopts a light with a high frequency stimulation (HFS) or a low frequency stimulation (LFS) to irradiate the designated area for generating a reaction from the designated area. Finally, the cover 4 is screw-connected to the large aperture portion 22 of the sleeve 2, so that the cover 4 can seal the sealing groove 35 and the large aperture portion 22.

As described above, the syringe 103 passes through the through hole 33 and the small aperture portion 21 and injects the designated area in the skull 101 with a carrier of photoreceptor gene by inserting the sleeve 2 in the drilled hole 102, and then the optogenetic stimulation is implemented on the designated area by using the illuminator 34 for generating a reaction from the designated area. Thus, the optogenetic stimulating element 3 and the cover 4 can be quickly and conveniently installed with or disassembled from the large aperture portion 2, and the operation time of syringe injection and phototherapeutic irradiation can be reduced, and the operation efficiency can be increased. Furthermore, the phototherapeutic irradiation of the optogenetic stimulation element 3 can be controlled to focus the neurons of the designated area, and not to affect other neurons surrounding the designated area. Compared with the electrical stimulation in prior art, the stationary trans-skull optogenetic stimulation module of the present invention has less side effects.

Figure 4:
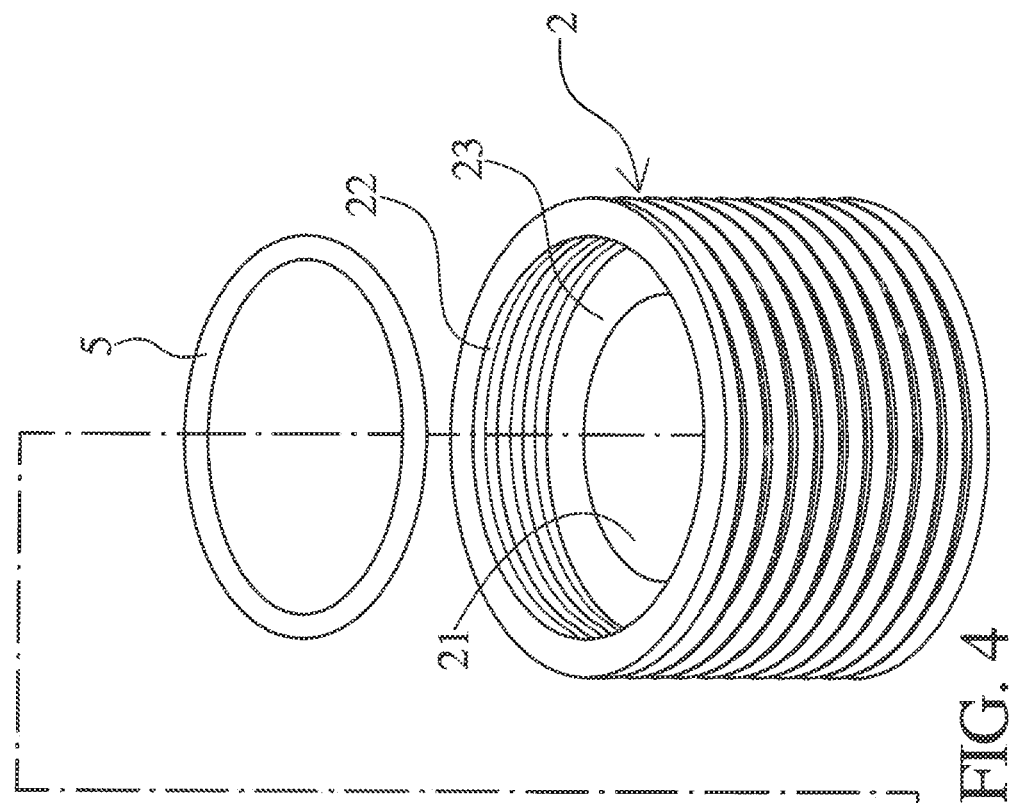
FIG. 4 is a schematic view of a stationary trans-skull optogenetic stimulation module according to a second embodiment of the present invention.
Figure 4:
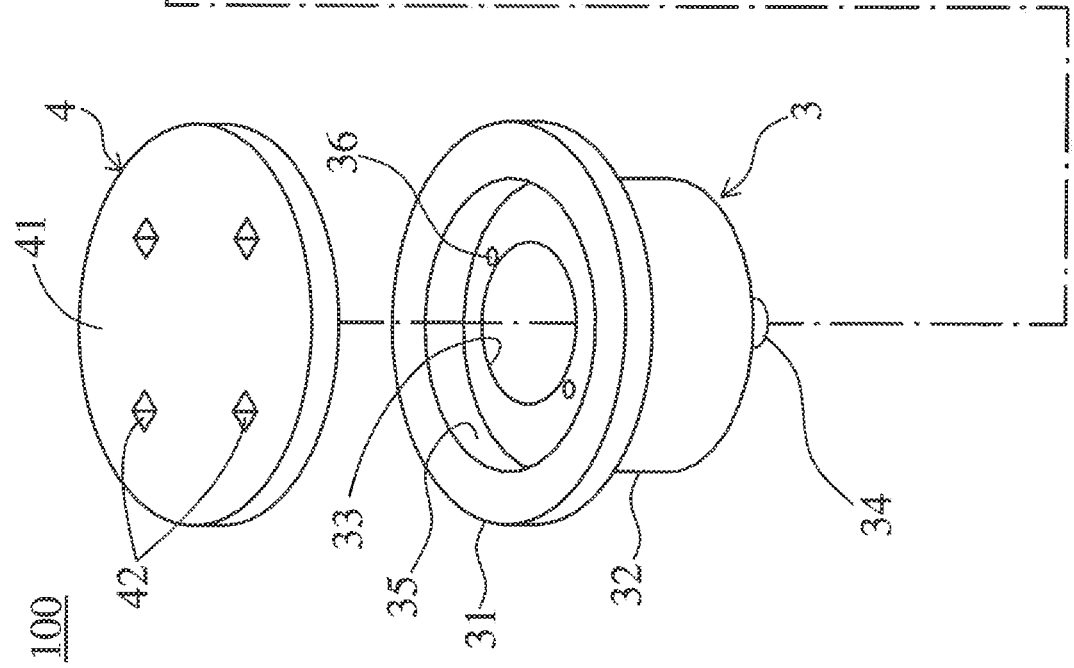
Figure 5:
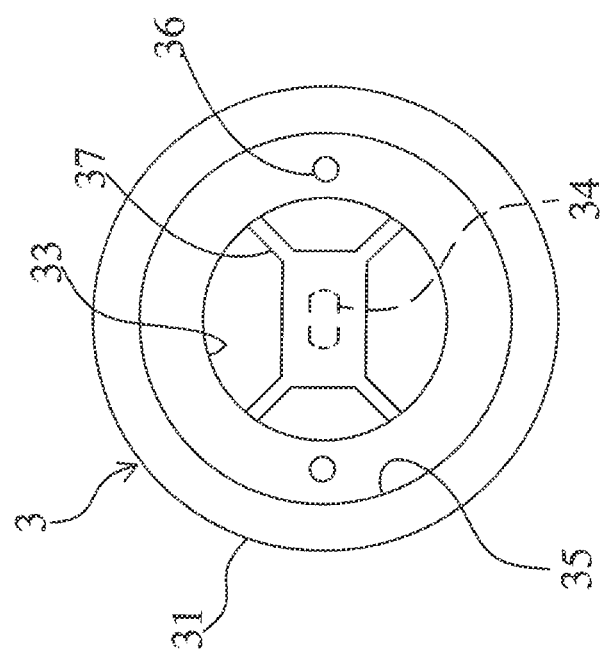
FIG. 5 is a top view of a stationary trans-skull optogenetic stimulation module according to the second embodiment of the present invention.

Referring to FIGS. 4 and 5, a stationary trans-skull optogenetic stimulation module according to a second embodiment of the present invention is illustrated, and is similar to the first embodiment, so that the second embodiment uses terms or numerals similar to those of the first embodiment. As shown, the difference of the second embodiment is that the illuminator 34 includes a light emitting diode (LED), and the optogenetic stimulation element 3 further includes a fixation base 37, wherein the fixation base 37 is disposed in the through hole, and configured to fix the illuminator 34, so that the illuminator 34 is located on an end of the through hole 33.

Figure 6:
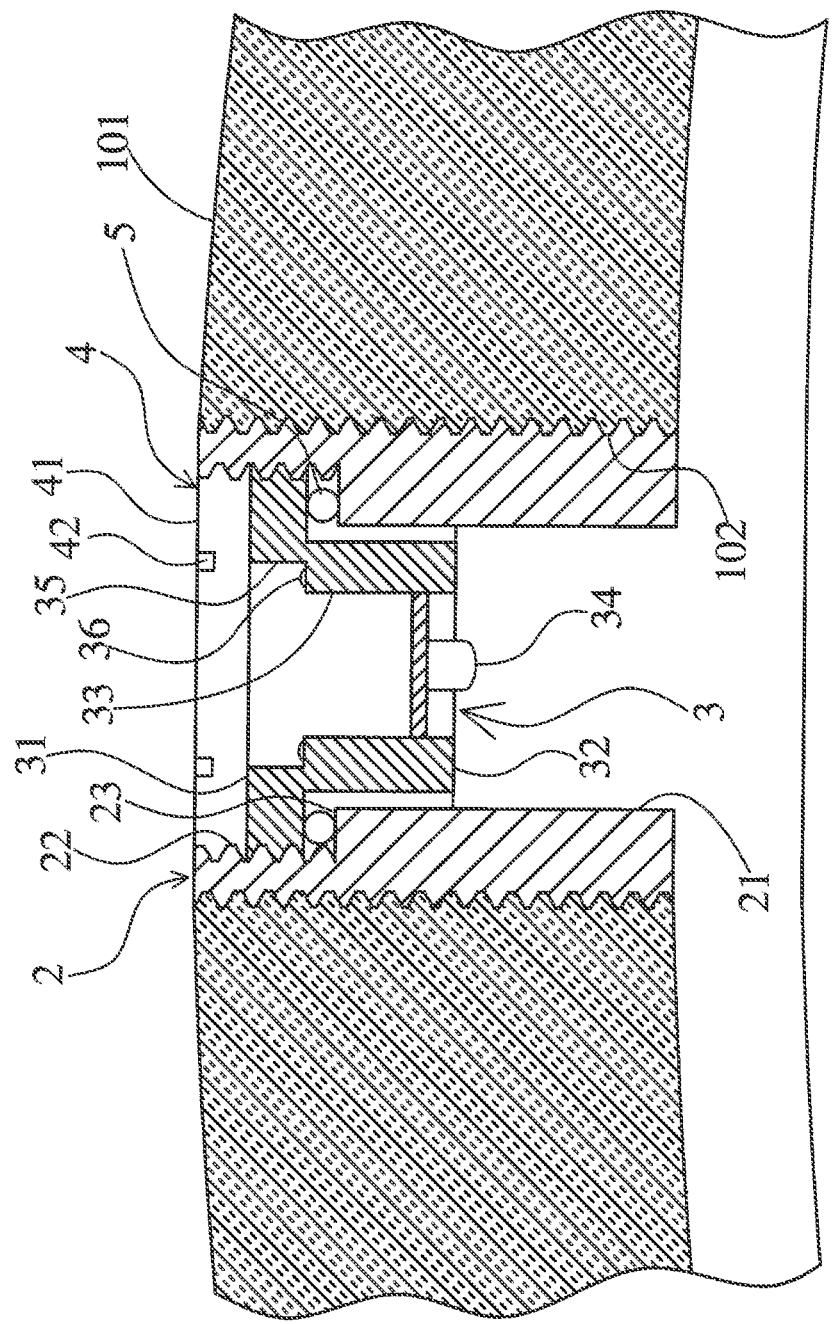
FIG. 6 is a sectional view of a stationary trans-skull optogenetic stimulation module according to the second embodiment of the present invention.
Figure 7:
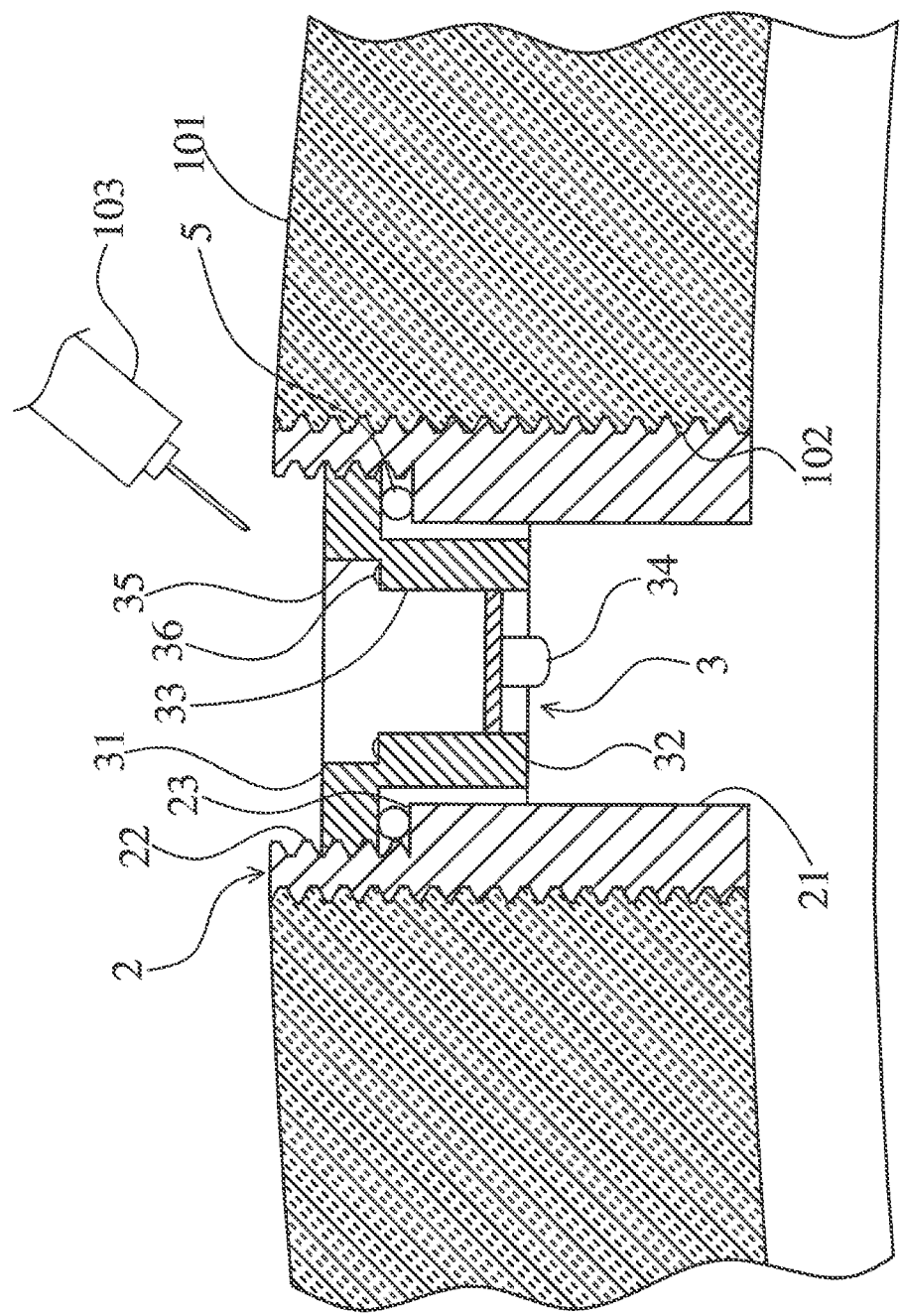
FIG. 7 is a sectional view of a stationary trans-skull optogenetic stimulation module for implementation according to the second embodiment of the present invention.

According to the described structure and referring to FIG. 6, the sleeve 2 is inserted and positioned in the drilled hole 102 of the skull 101 for sequentially screw-connecting to the optogenetic stimulation element 3 and the cover 4 in the large aperture portion 22 of the sleeve 2, and the cover 4 is covered on the connection portion 31 of the optogenetic stimulation element 3. Referring to FIG. 7, the depressed portions 42 can be engaged by a tool for unfastening the cover 4, and the cover 4 can be disassembled from the large aperture portion 22 of the sleeve 2. At this time, a syringe 103 can be used to pass through the through hole 33 and the small aperture portion 21, and injects a designated area in the skull 101 with a carrier of photoreceptor gene, and the optogenetic stimulation (phototherapeutic irradiation) is implemented on the designated area by using the illuminator 34 (LED package structure) located at the small aperture portion 21. Finally, the cover 4 is screw-connected to the large aperture portion 22 of the sleeve 2, so that the cover 4 can seal the sealing groove 35 and the large aperture portion 22.

As described above, the syringe 103 passes through the through hole 33 and the small aperture portion 21 and injects the designated area in the skull 101 with a carrier of photoreceptor gene by inserting the sleeve 2 in the drilled hole 102, and then the optogenetic stimulation is implemented on the designated area by using the illuminator 34 for generating a reaction from the designated area. Thus, the optogenetic stimulating element 3 and the cover 4 can be quickly and conveniently installed with or disassembled from the large aperture portion 2, and the operation time of syringe injection and phototherapeutic irradiation can be reduced, and the operation efficiency can be increased.

The present invention has been described with a preferred embodiment thereof and it is understood that many changes and modifications to the described embodiment can be carried out without departing from the scope and the spirit of the invention that is intended to be limited only by the appended claims.

What is claimed is:

1. A stationary trans-skull optogenetic stimulation module, comprising:
    a sleeve configured to be inserted and positioned in a drilled hole of a skull of a subject, and including a small aperture portion, a large aperture portion, and an inner flange, wherein the small aperture portion is communicated with the large aperture portion, and the inner flange is disposed between the small aperture portion and the large aperture portion;
    an optogenetic stimulation element including a connection portion configured to be detachably connected with the large aperture portion, an extension portion extended from the connection portion into the small aperture portion, a through hole passing through the connection portion and the extension portion, and an illuminator disposed on the extension portion; and
    a cover configured to be connected with the large aperture portion and cover the connection portion;
    wherein the connection portion is formed with a first external thread portion, the large aperture portion is formed with an internal thread portion, and the internal thread portion is configured to be screw-connected to the first external thread portion.

2. The stationary trans-skull optogenetic stimulation module according to claim 1, wherein the illuminator includes a light emitting diode or a spiral light strip.

3. The stationary trans-skull optogenetic stimulation module according to claim 2, wherein the illuminator is further covered with a biocompatible silicone layer.

4. The stationary trans-skull optogenetic stimulation module according to claim 1, wherein the optogenetic stimulation element further includes a fixation base disposed in the through hole, and configured to fix the illuminator.

5. The stationary trans-skull optogenetic stimulation module according to claim 1, wherein the optogenetic stimulation element further includes: a sealing groove formed on a top surface of the connection portion, and two conductive portions disposed in the sealing groove and electrically connected to the illuminator.

6. The stationary trans-skull optogenetic stimulation module according to claim 1, wherein the cover includes a top surface and at least one depressed portion formed on the top surface.

7. The stationary trans-skull optogenetic stimulation module according to claim 1, further comprising an elastic ring configured to be installed between the inner flange and the connection portion.

8. The stationary trans-skull optogenetic stimulation module according to claim 1, wherein the cover and the connection portion and the extension portion of the optogenetic stimulation element are made of titanium or titanium alloy.

9. The stationary trans-skull optogenetic stimulation module according to claim 1, wherein the cover includes a second external thread portion, and the internal thread portion is configured to be further screw-connected to the second external thread portion.

* * * * *